United States Patent
Groth et al.

(10) Patent No.: US 10,368,763 B2
(45) Date of Patent: Aug. 6, 2019

(54) APPARATUS AND METHOD FOR VISUALIZING A CONDUCTION TRACT OF HEART

(71) Applicant: KONINKLIJKE PHILIPS N.V., Eindhoven (NL)

(72) Inventors: Alexandra Groth, Hamburg (DE); Juergen Weese, Norderstedt (DE); Helko Lehmann, Strasbourg (FR); Hans Barschdorf, Dassendorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 883 days.

(21) Appl. No.: 14/380,982

(22) PCT Filed: Mar. 1, 2013

(86) PCT No.: PCT/IB2013/051634
§ 371 (c)(1),
(2) Date: Aug. 26, 2014

(87) PCT Pub. No.: WO2013/128415
PCT Pub. Date: Sep. 6, 2013

(65) Prior Publication Data
US 2015/0025364 A1     Jan. 22, 2015

Related U.S. Application Data

(60) Provisional application No. 61/605,823, filed on Mar. 2, 2012.

(51) Int. Cl.
   *A61B 5/00*        (2006.01)
   *A61B 5/04*        (2006.01)
(Continued)

(52) U.S. Cl.
   CPC ........ *A61B 5/04011* (2013.01); *A61B 5/0066* (2013.01); *A61B 5/0084* (2013.01);
(Continued)

(58) Field of Classification Search
   CPC ... A61B 5/04011; A61B 5/0402; A61B 5/042; A61B 5/055; A61B 5/061; A61B 5/6852;
(Continued)

(56) References Cited

U.S. PATENT DOCUMENTS

2005/0203375 A1    9/2005   Willis
2007/0049826 A1*   3/2007   Willis ................ A61B 1/00147
                                                          600/439

(Continued)

FOREIGN PATENT DOCUMENTS

WO     2010062218 A1    6/2010

OTHER PUBLICATIONS

Olivier Ecabert et al, "Automatic Model-Based Segmentation of the Heart in CT Images", IEEE Transactions on Medical Imaging, vol. 27, No. 9, Sep. 2008, pp. 1189-1201.

(Continued)

*Primary Examiner* — Peter Luong

(57) ABSTRACT

An apparatus, a method and a computer program for visualizing a conduction tract of a heart include adapting a generic heart model to match geometrical data of a patient's heart, where model data, corresponding to the generic heart model and indicating a shape and/or position of the conduction tract, is modified in accordance to the adaptation of the generic heart model. The modification of the model data is further refined based on electrophysiological data of the patient to produce refined model data, and the refined model data is used for generating a visualization of a refined model heart indicating a refined shape and/or refined position of the conduction tract of the patients heart.

12 Claims, 2 Drawing Sheets

(51) Int. Cl.
*A61B 8/00* (2006.01)
*A61B 5/0402* (2006.01)
*A61B 5/042* (2006.01)
*G06T 17/00* (2006.01)
*A61B 5/055* (2006.01)
*A61B 5/06* (2006.01)
*A61B 6/03* (2006.01)

(52) U.S. Cl.
CPC ............ *A61B 5/0402* (2013.01); *A61B 5/042* (2013.01); *A61B 5/055* (2013.01); *A61B 5/061* (2013.01); *A61B 5/743* (2013.01); *A61B 5/7425* (2013.01); *A61B 6/032* (2013.01); *A61B 8/44* (2013.01); *A61B 8/445* (2013.01); *G06T 17/00* (2013.01); *A61B 5/6852* (2013.01); *A61B 5/6886* (2013.01); *A61B 2576/023* (2013.01); *G06T 2210/41* (2013.01)

(58) Field of Classification Search
CPC ..... A61B 5/6886; A61B 5/7425; A61B 5/743; A61B 6/032; A61B 2576/023; G06T 17/00; G06T 2210/41
USPC ........................................................ 600/424
See application file for complete search history.

(56) References Cited

U.S. PATENT DOCUMENTS

| | | |
|---|---|---|
| 2007/0078325 A1 | 4/2007 | Fuimaono |
| 2008/0208068 A1 | 8/2008 | Robertson |
| 2008/0214945 A1 | 9/2008 | Koertge et al. |
| 2008/0287803 A1 | 11/2008 | Li et al. |
| 2010/0030107 A1* | 2/2010 | Hancock ............ A61B 10/0233 600/567 |
| 2010/0191131 A1 | 7/2010 | Revishvili et al. |
| 2011/0224962 A1 | 9/2011 | Goldberger et al. |
| 2013/0197881 A1* | 8/2013 | Mansi ................ G06F 17/5009 703/2 |

OTHER PUBLICATIONS

R. Fenici et al, "From 3D to 4D imaging: is that useful for interventional cardiac electrophysiology?", Proceedings of the 29th Annual International Conference of the IEEE EMBS, Cite Internationale, Lyon, France, Aug. 23-26, 2007, SaD3.1, pp. 5995-5998.

M.W. Krueger et al, "Semi-automatic segmentation of sinus node, Bachmann's Bundle and Terminal Crest for patient specific atrial models", Proc. of World Congress on Medical Physics and Biomedical Engineering, IFMBE Proceedings, 25(4), 2010, pp. 673-676.

M. Sermesant et al, "An Electromechanical Model of the Heart for Image Analysis and Simulation", IEEE Transactions on Medical Imaging, vol. 25, No. 5, May 2006, pp. 612-625.

M. Sermesant et al, "Patient-specific electromechanical models of the heart for prediction of pacing acute effects in CRT: A preliminary clinical validation", Medical Image Analysis 16, 2012, pp. 201-215.

Sermesant, M. et al, "Simulation of cardiac pathologies using an electromechanical biventricular model and XMR interventional imaging", Medical Image Analysis, vol. 9. 2005, pp. 467-480.

Neher, Peter et al, "Automatic Segmentation of Cardiac CTs—Personalized Atrial Models Augmented with Electrophysiological Structures", Institute of Biomedical Engineering, Karlsruhe Institute of Technology (KIT), Germany, Philips Research Hamburg, Germany, pp. 80-87, 2011.

\* cited by examiner

APPARATUS AND METHOD FOR VISUALIZING A CONDUCTION TRACT OF HEART

CROSS-REFERENCE TO PRIOR APPLICATIONS

This application is the U.S. National Phase application under 35 U.S.C. § 371 of International Application Serial No. PCT/IB2013/051634, filed on Mar. 1, 2013, which claims the benefit of U.S. Application Ser. No. 61/605,823, filed on Mar. 2, 2012. These applications are hereby incorporated by reference herein.

FIELD OF THE INVENTION

The invention relates to an apparatus, a method and a computer program for visualizing a conduction tract of a heart.

BACKGROUND OF THE INVENTION

US 20110224962 A1 is related to an electrophysiological testing simulation for medical condition determination, wherein an aim is to identify scar tissue. This is done by thresholding, wherein scar tissue is identified due to different intensities. The eventual simulation is provided only for diagnosis purposes.

US 20100191131 A1 is related to a method of noninvasive electrophysiological study of the heart, wherein activation maps are obtained of a surface heart model, which might be used by a medical practitioner to estimate where conduction tracts or structures might be located.

In electrophysiological procedures, a scar in the heart tissue is created, for example, by ablation to interrupt an abnormal electrical conduction e.g. in case of atrial flutter. In the ablation procedure, it is important to know the location of the physiological conduction tracts like the Bachmann's bundle and Purkinje fibres since they have a specific function and their ablation would irrevocably destroy the normal conduction pathways of the heart. This especially holds for the Bachmann's bundle which originates in the sinoatrial node and is therefore the only tract that conducts action potentials to the left atrium.

In addition, there are also cases in which a therapy is provided involving voluntarily ablating a conduction tract of the heart. An example of such therapy is related to atrioventricular nodal reentrant tachycardia (AVNRT) involving usually two anatomical pathways, a fast pathway and a slow pathway (both in the right atrium). A successful catheter ablation of the slow pathway may result in curing the patient from AVNRT.

Currently, no information about the physiological conduction tracts like the Bachmann's bundle is available to the physician in an ablation procedure since these structures are neither visible on intra-interventionally acquired x-ray images nor on pre-interventionally acquired CT and MR images.

SUMMARY OF THE INVENTION

It is an object of the present invention to provide an apparatus, a method and a computer program for visualization of a conduction tract of the heart of a patient, wherein this visualization is helpful in avoiding or finding the conduction tract in, for example, an invasive procedure like ablation of heart tissue.

In a first aspect of the present invention an apparatus for visualizing a conduction tract of a heart, comprising a storage unit for a generic heart model and model data, the generic heart model representing at least a portion of an actual heart, and the model data corresponding to the generic heart model indicating a shape and/or position of the conduction tract in the heart model, an input unit for obtaining geometrical data of a patient's heart corresponding to the generic heart model and electrophysiological data of the patient, a model adapting unit for adapting the generic heart model to match geometrical data inputted to the input unit, a model data modifying unit for modifying the model data to reflect the adapting provided by the model adapting unit, a model refining unit for refining the modified model data based on the electrophysiological data, and a generation unit for generating a visualization of the conduction tract using the refined model data.

In addition to anatomical images, electrophysiological measurement resulting, for example, from electroanatomical mapping is already conventionally available. Systems like CARTO from Biosense Webster or Ensite NavX are able to display activation timing and electrical potentials to the physician. However, from such data a physician still cannot see the location of the conduction tracts either.

One of the eventual purposes of the present invention is to allow for a determination the patient specific shape and location of the structures responsible for the electrophysiological conduction of the heart and display them to the physician.

To this aim, a generic model with encoded conduction structures is adapted to the patient specific heart shape using pre-interventional image data. As a result, the general mean shape and location of the conduction structures is transferrable to the patient's geometry.

However, the generic model and its adaptation alone do not sufficiently allow for a correct localization of the actual conduction tracts.

It is further realized that electrophysiological data may be used to further personalize the shape and location of the conduction structures, at least in and around the area where such electrophysiological data are available. In the process, the location and shape of the conduction structures are refined such that the modified model and the actual heart may be assumed as corresponding sufficiently.

It is to be noted that the general approach of adapting a generic model to image data (or the like) of an actual patient is an approach with which the skilled person is well familiar, so that there is no need for a detailed discussion here.

The adaptation of the generic model to the actual heart and the modification of the model data may be provided simultaneously if the model data is incorporated into the generic model to such an extent that the adaption directly results also in the corresponding modification. Nevertheless, the model data may also be provided in a form that there is a relation between a detail (or group of details) of the model data and a detail (or group of details) of the model of the heart. Such relation may be that a particular point of the conduction tract is related to a node of the heart model, a point on a line between nodes of the heart model or a point inside a plane (or geometrical shape) defined by multiple nodes of the heart model. The same applies to lines or other features of the model data.

In order to provide a visualization which is helpful in avoiding or finding the conduction tract in, for example, an invasive procedure like ablation of heart tissue, a generic heart model is adapted to geometrical data of the patient's heart, wherein model data indicating a shape and/or position of the conduction tract is modifying in accordance to the adaptation. The modification of the model data is further refined based on electrophysiological data and the refined model is used for generating a visualization.

In a preferred embodiment, the model refining unit includes a simulation unit for calculating simulated electrophysiological data corresponding to the modified model data, a comparison unit for comparing the simulated electrophysiological data to the inputted electrophysiological data and for outputting a comparison result, and a first refinement unit for refining the modified model data based on the comparison result.

The refinement of the model, which may be provided iteratively, is checked with the available data and in particular there is a comparison between actually measured electrophysiological data and a simulation result based on the current version of the refined model.

In a preferred embodiment the model refining unit includes an extraction unit for extracting characteristic features from the electrophysiological data, and a second refinement unit for refining the modified model data based on the characteristic features.

For example in the case of an electroanatomical mapping being included in the electrophysiological data, there might be characteristic features related to particular aspects of the conduction tract, which on their own may not be sufficient for completely identifying or localizing a part of the conduction tract of the heart, even though such features are sufficient for refining, i.e. adapting, the model. The position of, for example, the Bachmann's bundle may be deducted roughly as a medium line from the corresponding area of the electroanatomical mapping, wherein furthermore an estimated position of the coronary sinus is obtainable from the corresponding area in the mapping.

In a modification of the above embodiment, the extraction unit is arranged for extracting a minimum of an electrical activation time, and wherein the second refinement unit is arranged for refining the location of the end conduction tract based on the extracted electrical activation time.

The knowledge about the relation between the end conduction tract and the minimum of the electrical activation time may also be used for refining the model.

In a preferred embodiment, the model refining unit is arranged for refining the model data in an iterative manner.

In particular in the context of using simulations based on the current version of the (refined) model, the degree of refinement usually increased with a number of iterations, i.e. the use of a refined model for generating an updated simulation which is then used for an additional refinement following by a further generating of a simulation. Nevertheless, also in other contexts, an iterative approach provides advantageous. A first, rather coarse, refinement is followed by a finer refinement, wherein the combination of first and second refinement may require less computational load than a combined refinement.

The above-mentioned approaches on refinement may be used in combination or separately (i.e. only one particular refinement approach is used while the other is not implemented).

In a preferred embodiment, the generation unit is arranged for generating the visualization of the conduction tract by superposing a representation of the refined model data on geometrical data and/or by displaying the representation of the refined model data separately.

Depending on the user's intention and preferences a superposition of a graphical visualization of the refined model data on image data of the heart, a presentation just the refined model data in graphical form, and/or a combination of such displays may be provided. The visualization may be two-dimensional, three-dimensional and/or four-dimensional (i.e. three-dimensional data changing over time).

In a preferred embodiment, the geometrical data includes two-dimensional data and/or three-dimensional data and/or four-dimensional data, in particular data obtained by radiography, tomography and/or magnetic resonance imaging.

Basically any kind of geometrical data which is obtainable for the heart may be used in the context of the present invention.

In a preferred embodiment, the electrophysiological data includes an electroanatomical mapping of the heart and/or body-surface-potential data of the patient. The electroanatomical mapping is obtained by an invasive procedure, while the body-surface-potential data are obtainable in a non-invasive way.

In a preferred embodiment, the visualizing apparatus of the present invention is included in an apparatus for assisting an electrophysiological procedure, which further includes an instrument position obtainment unit for obtaining position data on an medical instrument to be used in the electrophysiological procedure, a distance calculation unit for calculating, during the electrophysiological procedure, a distance between the medical instrument and a position of the conduction tract according to the refined model data, and an indication unit for indicating the calculated distance.

The apparatus for assisting the electrophysical procedure uses the refined model and the visualization to improve the practitioner's amount of information on the current status of the procedure and the situation inside the patient's body.

One possibility for indicating the calculated distance is just an acoustical or optical signal indicating that the calculated distance is smaller than a predetermined threshold.

Another possibility is an outputting of a signal which changes in relation to the distance, e.g. an actual display of the distance (e.g. in cm or mm) or a sound or sound modulation the frequency of which is related to the distance.

A further possibility includes a display of a representation of the instrument superposed in a display representing the model data.

In a preferred embodiment, the apparatus for assisting the electrophysical procedure further includes an instrument control unit for allowing and/or prohibiting a function of the medical instrument based on the calculated distance.

The instrument control unit further reduces risks involved with the electrophysical procedure by limiting the active operation of the medical instrument to an area defined by means of the obtained refined model.

In a further aspect of the present invention a method for visualizing a conduction tract of a heart is presented, comprising the steps: providing a generic heart model and corresponding model data indicating a shape and/or position of the conduction tract in the heart model, the generic heart model representing at least a portion of an actual heart, obtaining geometrical data of a patient's heart corresponding to the generic heart model, adapting the generic heart model to match the obtained geometrical data and modifying the model data to reflect the adapting, obtaining electrophysiological data of the patient, refining the modified model data based on the obtained electrophysiological data, and generating a visualization of the conduction tract using the refined model data.

In a further aspect of the present invention a computer program for visualizing a conduction tract of a heart is presented, the computer program comprising program code means for causing the method according to the invention to be carried out when the computer program is run on a computer.

It shall be understood that the apparatus for visualizing a conduction tract of a heart, the method for visualizing a conduction tract of a heart, and the computer program have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
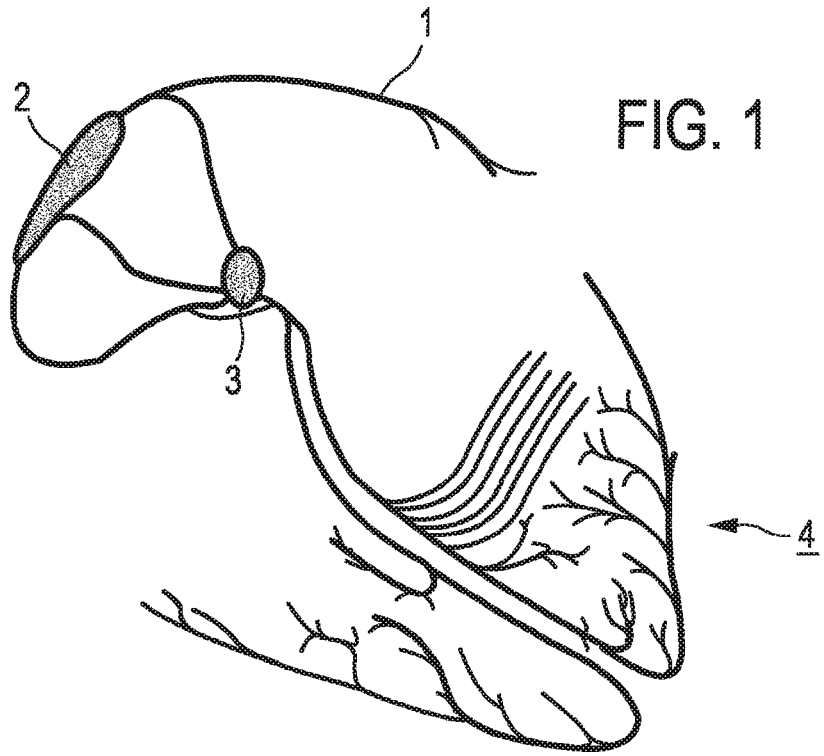
FIG. 1 shows a schematic representation of conduction tracts of a human heart.

FIG. 1 shows a schematic representation of conduction tracts of a human heart, illustrating, amount others, the position of the Bachmann's bundle 1, the sinoatrial node 2, the atrioventricular node 3 and Purkinje fibers 4 as examples for conductions tracts.

Figure 2:
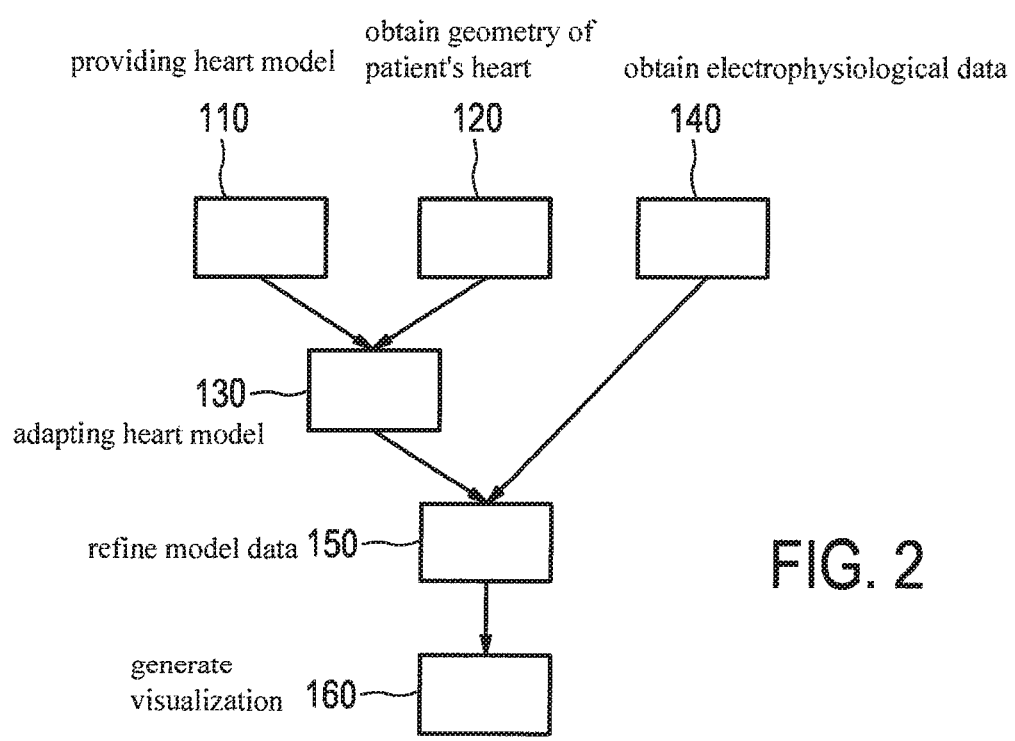
FIG. 2 shows a flow diagram illustrating an embodiment of a method for visualizing a conduction tract of a heart according to the invention.

FIG. 2 shows a flow diagram illustrating an embodiment of a method for visualizing a conduction tract of a heart. In the exemplary embodiment, the shape (or at least characteristic landmarks that allow to reconstruct the shape) of the structures responsible for the electrophysiological conduction is encoded in the models of a cardiac segmentation framework (for details, see, for example, M. W. Krueger, F. M. Weber, G. Seemann, O. Dössel, "Semi-automatic segmentation of sinus node, Bachmann's Bundle and Terminal Crest for patient specific atrial models", Proc. of World Congress on Medical Physics and Biomedical Engineering, IFMBE Proceedings, 25(4), 2010, 673-676).

The above is included in Step 110, in which therefore a generic heart model is provided together with corresponding model data indicating a shape and/or position of the conduction tract in the heart model. It is to be noted that the generic heart model does not necessarily represent a complete heart and may also refer just to a part or portion of a heart.

In a further step 120, the geometry of the patient's heart (or at least the relevant portion of the heart corresponding to the model) is obtained. This is done by means of the image generation process of computer tomography (CT) allowing for a three-dimensional image. Alternatively, other methods like magnetic resonance imaging (MR) may also be used. In addition, combinations of such methods are also possible.

In step 130, the generic heart model provided in step 110 is adapted to match the obtained geometrical data from step 120. The adaptation of such a model of an organ is well known to the skilled person (see for example: O. Ecabert, J. Peters, H. Schramm, C. Lorenz, J. von Berg, M. J. Walker, M. Vembar, M. E. Olszewski, K. Subramanyan, G. Lavi, J. Weese, "Automatic Model-based Segmentation of the Heart in CT Images", IEEE Transactions on Medical Imaging 2008, 27(9), 1189-1201 or P. Neher, H. Barschdorf, S. Dries, F. M. Weber, M. W. Krueger, O. Dössel, C. Lorenz, "Automatic Segmentation of Cardiac CTs—Personalized Atrial Models Augmented with Electrophysiological Structures", submitted to FIMH 2011). Basically any of the known adaption method may be applied here. Therefore, a further discussion of details of such adaption is omitted here. Step 130 further includes a modifying of the model data to reflect the adapting. In other words, the change in the shape of the generic model of the heart provided for adapting the generic model to match the image data of the actual heart is provided correspondingly also to the model data.

In step 140, electroanatomical mapping results (measured with CARTO (see http://www.biosensewebster.com/products/navigation/) or Ensite NavX (see http://www.sjmprofessional.com/Products/US/Mapping-and-Visualization/EnSite-NavX-Navigation-and-Visualization-Technology.aspx) are used to further refine the model of the heart and the modified model data. This is done by extracting characteristic features from the measured electrical signals and their spatial distribution. Here, minima of the electrical activation time are be used to refine the location of the end conduction tracts.

As an alternative or in combination, the heart shape and the location of the conduction structures are used to perform simulations of the electrical signal propagation (see M. Sermesant, H. Delingette, N. Ayache, "An Electromechanical Model of the Heart for Image Analysis and Simulation", IEEE TRANSACTIONS ON MEDICAL IMAGING 2006, 25(5), 612-625, where the Purkinje network terminations are used as an initial condition for simulation). To this aim, existing programs like CMISS (interactive computer program for Continuum Mechanics, Image analysis, Signal processing and System Identification) (http://www.cmiss.org/), Continuity (http//:www.continuity.ucsd.edu/Continuity) or CHASTE (http://web.comlab.ox.ac.uk/projects/chaste-cardiac-hpc/) can be used. The simulations are compared to the measured signals (e.g. globally or only in specific areas of the heart (e.g. close to the end of the fast conduction tracts) and the parameters defining the geometry of the (representation of the) conduction tract, i.e. the model data, are modified in an iterative process until an optimal agreement between the measurements and the simulation is obtained.

As an alternative to the invasive electroanatomical mapping, also a noninvasive approach obtaining body-surface potentials may be used. Furthermore, both ways of obtaining electrophysiological data may be used in combination.

Finally, step 160, the adapted and refined heart model with the physiological conduction tracts (by means of the modified and refined model data) is displayed during an intervention, e.g. in a separate viewport or as an overlay onto x-ray images, generating a visualization of the conduction tract using the refined model data.

During a cardiac ablation procedure, the present invention allows for an information of the physician regarding that and what physiological conduction tract is close to the ablation position or may be affected if ablation at this specific point is carried out. This can be realized by mapping the position of the ablation catheter to the heart model including the conduction tracts coded in the modified and refined model data.

In FIG. 2, the steps 110, 120 and 140 are indicated in parallel. However, this does not means that these steps necessarily have to be provided in parallel. It is also possible, and probably the case in most implementations, that the steps 110, 120 and 140 are carried out in some sort of sequence, wherein, for example, step 110 is followed by step 120 and step 140 follows step 130.

Figure 3:
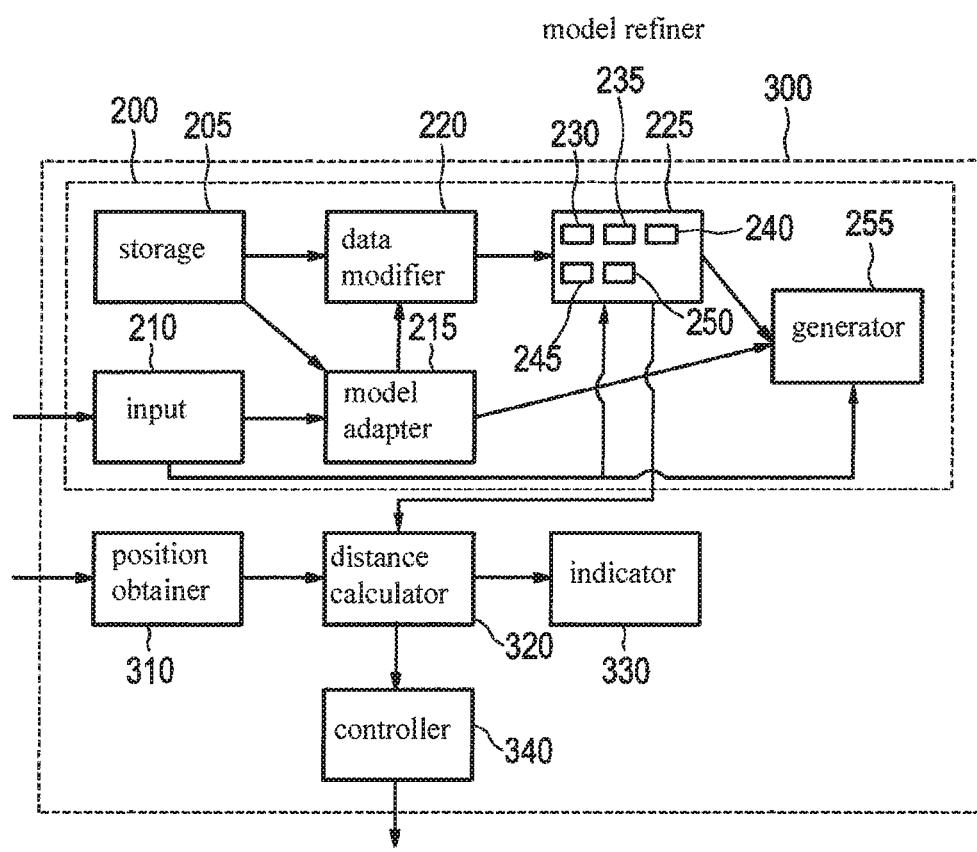
FIG. 3 shows a schematic illustration of an embodiment of an apparatus for visualizing a conduction tract according to the invention included in an apparatus for assisting an electrophysiological procedure.

FIG. 3 shows a schematic illustration of an embodiment of an apparatus 200 for visualizing a conduction tract according to the invention included in an apparatus 300 for assisting an electrophysiological procedure.

The apparatus 200 for visualizing includes a storage unit 205, an input unit 210, a model adapting unit 215, a model data modifying unit 220, a model refining unit 225 and a generation unit 255.

The storage unit 205 stores a generic heart model and model data. The generic heart model represents at least a portion of an actual heart. The model data corresponds to the generic model and indicates shapes and positions of conduction tracts of the heart (see FIG. 1).

The input unit 210 is provided for receiving geometrical data of a patient's heart to be used for adapting the generic model and thus modifying the model data.

The model adapting unit 215 receives the obtained geometrical data from the input unit and the generic heart model from the storage unit 205. The model adapting unit 215 adapts the generic heart model in a known way in order to have the adapted heart model matching the obtained geometrical data.

The model data modifying unit 220 receives the model data from the storage unit 205 and information on the adaptation of the heart model. Based on this information, the model data is modified in order to reflect the adaptation in modified model data.

The modified model data is provided to the model refinement unit 225, which also receives electrophysiological data obtained by the input unit 210.

The model refinement unit 225 includes a simulation unit 230, a comparison unit 235, a first refinement unit 240, an extraction unit 245 and a second refinement unit 250.

Based on the modified model data, the simulation unit 230 calculates simulated electrophysiological data to be compared to the obtained electrophysiological data by the comparison unit 235, wherein the result of the comparison is then used by the first refinement unit 240 to refine the model data.

In parallel to the above, the extraction unit 245 processes the electrophysiological data in order to extract characteristic features, which are used by the second refinement unit 250 for refining the model data.

The above two processes may be used iteratively for improved results. However, it is also possible to provide the processes separately and to combine the results (e.g. by averaging).

The refined model data is provided to the generation unit 255, which generates a visualization of the conduction tracts based on the refined model data.

In addition to the apparatus 200 for visualizing, the apparatus 300 for assisting also includes an instrument position obtainment unit 310, a distance calculation unit 320, an indication unit 330 and an instrument control unit 340.

The instrument position obtainment unit 310 receives information on the position of the instrument or instruments used in the electrophysiological procedure (not shown) and forwards this information to the distance calculation unit 320, which also receives relevant information from the model data refinement unit 225. The available information is used for calculating a distance between the instrument(s) and the conduction tracts. The calculation result, i.e. the distance information, is provided to the indication unit 330 and the instrument control unit 340. The indication unit 330 indicates the calculated distance. In order to further avoid accidental misuse of the instrument (e.g. the ablation of a conduction tract), the instrument control unit 340 prohibits the activation of the instrument if the distance is smaller than a predetermined threshold distance, wherein this prohibition may be cancelled by an overriding control by the user of the instrument, i.e. the medial practitioner.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Operations like model modification, model refinement, visualization generation, calculating simulated data, comparing measured data and calculated simulation data, and extracting of features from data can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

The invention claimed is:

1. An apparatus for visualizing a conduction tract of a heart a subject, comprising:
    a storage configured to store a generic heart model and model data, the generic heart model representing at least a portion of an actual heart, and the model data corresponding to the generic heart model indicating at least one of a shape and a position of the conduction tract in the generic heart model;
    an input configured to receive geometrical data of the heart of the subject corresponding to the generic heart model and electrophysiological data of the subject;
    a model adapter configured to adapt the generic heart model to match the geometrical data inputted to the input to generate an adapted generic heart model;
    a model data modifier configured to modify the model data into modified model data to reflect the adapted generic heart model provided by the model adapter indicating at least one of an adapted shape and an adapted position of the conduction tract in the generic heart model;
    a model refiner configured to refine the modified model data into refined model data indicating at least one of a refined shape and a refined position of the conduction tract in the generic heart model based on the electrophysiological data; and
    a generator configured to generate a visualization of the conduction tract, having the at least one of the refined shape and the refined position, using the refined model data.

2. The apparatus as defined in claim 1, wherein the model refiner comprises:

a simulator configured to calculate simulated electrophysiological data corresponding to the modified model data;

a comparator configured to compare the simulated electrophysiological data to the electrophysiological data received by the input and to output a comparison result; and a comparison refiner configured to refine the modified model data based on the comparison result.

3. The apparatus as defined in claim 1, wherein the model refiner comprises:

an extractor configured to extract characteristic features from the electrophysiological data; and a feature refiner configured to refine the modified model data based on the characteristic features.

4. The apparatus as defined in claim 3, wherein the extractor is configured to extract a minimum of an electrical activation time, and wherein the feature refiner is configured to refine a location of an end conduction tract based on the electrical activation time extracted by the extractor.

5. The apparatus as defined in claim 1, wherein the model refiner is configured to refine the model data in an iterative manner.

6. The apparatus as defined in claim 1, wherein the generator is configured to generate the visualization of the conduction tract, having the at least one of the refined shape and the refined position, at least one of by superposing a representation of the refined model data on geometrical data and by displaying the representation of the refined model data separately.

7. The apparatus as defined in claim 1, wherein the geometrical data includes at least one of two-dimensional data, three-dimensional data and four-dimensional data, and wherein the geometrical data is obtained by at least one of radiography, tomography and magnetic resonance imaging.

8. The apparatus as defined in claim 1, wherein the electrophysiological data includes at least one of an electroanatomical mapping of the heart and a body-surface-potential data of the subject.

9. An apparatus for assisting an electrophysiological procedure, comprising:

a visualizing apparatus as defined in claim 1, and an instrument position obtainer configured to obtain position data of a medical instrument to be used in the electrophysiological procedure;

a distance calculator configured to calculate, during the electrophysiological procedure, a distance between the medical instrument and a position of the conduction tract according to the refined model data; and an indicator configured to indicate the distance calculated by the distance calculator.

10. The apparatus as defined in claim 9, further comprising:

an instrument controller configured to at least one of allow and prohibit a function of the medical instrument based on the distance calculated by the distance calculator.

11. A method for visualizing a conduction tract of a heart of a subject, the method comprising acts of:

providing a generic heart model and model data corresponding to the generic heart model indicating at least one of a shape and a position of the conduction tract in the generic heart model, the generic heart model representing at least a portion of an actual heart;

obtaining geometrical data of the heart of the subject corresponding to the generic heart model;

adapting the generic heart model to match the geometrical data obtained in the obtaining geometrical data act, and modifying the model data into modified model data to reflect the adapting act indicating at least one of an adapted shape and an adapted position of the conduction tract in the generic heart model;

obtaining electrophysiological data of the subject;

refining the modified model data into refined model data indicating at least one of a refined shape and a refined position of the conduction tract in the generic heart model based on the electrophysiological data obtained by the act of obtaining electrophysiological data; and generating a visualization of the conduction tract, having the at least one of the refined shape and the refined position, using the refined model data.

12. A non-transitory computer readable medium comprising computer instructions which, when executed by a processor, configure the processor to perform a method for visualizing a conduction tract of a heart, the method comprising acts of:

providing a generic heart model and model data corresponding to the generic heart model indicating at least one of a shape and a position of the conduction tract in the generic heart model, the generic heart model representing at least a portion of an actual heart;

obtaining geometrical data of the heart of the subject corresponding to the generic heart model;

adapting the generic heart model to match the geometrical data obtained in the obtaining geometrical data act, and modifying the model data into modified model data to reflect the adapting act indicating at least one of an adapted shape and an adapted position of the conduction tract in the generic heart model;

obtaining electrophysiological data of the subject;

refining the modified model data into refined model data indicating at least one of a refined shape and a refined position of the conduction tract in the generic heart model based on the electrophysiological data obtained by the act of obtaining electrophysiological data; and generating a visualization of the conduction tract, having the at least one of the refined shape and the refined position, using the refined model data.

* * * * *